United States Patent
Jamous et al.

(10) Patent No.: US 10,492,823 B2
(45) Date of Patent: Dec. 3, 2019

(54) TISSUE-REMOVING CATHETER AND METHOD OF REMOVING TISSUE

(71) Applicant: Medtronic Vascular, Inc., Santa Rosa, CA (US)

(72) Inventors: Aram Jamous, Athenry (IE); Colin Meade, Westmeath (IE); Grainne Carroll, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 192 days.

(21) Appl. No.: 15/672,130

(22) Filed: Aug. 8, 2017

(65) Prior Publication Data

US 2019/0046228 A1    Feb. 14, 2019

(51) Int. Cl.
| | |
|---|---|
| A61B 17/3207 | (2006.01) |
| A61B 1/313 | (2006.01) |
| A61B 17/22 | (2006.01) |
| A61B 17/32 | (2006.01) |
| A61B 17/3203 | (2006.01) |

(52) U.S. Cl.
CPC .... *A61B 17/320758* (2013.01); *A61B 1/3137* (2013.01); *A61B 17/320783* (2013.01); *A61B 17/32037* (2013.01); *A61B 2017/22038* (2013.01); *A61B 2017/320004* (2013.01); *A61B 2017/320078* (2017.08)

(58) Field of Classification Search
CPC .............................................. A61B 17/320758
See application file for complete search history.

(56) References Cited

U.S. PATENT DOCUMENTS

| | | | |
|---|---|---|---|
| 6,375,609 B1 | 4/2002 | Hastings et al. | |
| 9,241,733 B2 | 1/2016 | Olson | |
| 2007/0239182 A1* | 10/2007 | Glines | A61B 17/22012 606/159 |
| 2008/0065125 A1* | 3/2008 | Olson | A61B 17/320758 606/159 |
| 2008/0097298 A1* | 4/2008 | Fisher | A61B 17/320758 604/103.04 |
| 2009/0234378 A1* | 9/2009 | Escudero | A61B 17/320758 606/180 |

(Continued)

FOREIGN PATENT DOCUMENTS

WO    2008021541 A2    2/2008

OTHER PUBLICATIONS

EP18187044.A Extended European Search Report, dated Dec. 11, 2018 (Year: 2018).*

*Primary Examiner* — Meredith Weare

(57) ABSTRACT

A tissue-removing catheter includes an elongate body having proximal and distal end portions and a motor fixed to the distal end portion of the elongate body. A tissue-removing element is mounted on the motor to be driven in rotation by the motor about a drive axis. In some embodiments, the tissue-removing element includes a receptacle that receives the motor therein. The tissue-removing element can include a distal tip that extends distally beyond the motor to define the distal end of the catheter. The motor can be controlled using an actuator located outside the body. And in some embodiments, use of the catheter involves adjusting the rotational speed of the tissue-removing element using the actuator.

18 Claims, 2 Drawing Sheets

(56) References Cited

U.S. PATENT DOCUMENTS

2011/0105845 A1* 5/2011 Gordon .............. A61B 1/00094
600/156
2012/0016395 A1 1/2012 Olson
2015/0216553 A1* 8/2015 Kessler .......... A61B 17/320758
606/159

* cited by examiner

TISSUE-REMOVING CATHETER AND METHOD OF REMOVING TISSUE

FIELD

The present disclosure generally relates to a tissue-removing catheter and method of removing tissue.

BACKGROUND

Tissue-removing catheters are used to remove unwanted tissue in body lumens. As an example, atherectomy catheters are used to remove material from a blood vessel to open the blood vessel and improve blood flow through the vessel.

SUMMARY

A tissue-removing catheter includes an elongate body having proximal and distal end portions and a motor fixed to the distal end portion of the elongate body. A tissue-removing element is mounted on the motor to be driven in rotation by the motor about a drive axis. In some embodiments, the tissue-removing element includes a receptacle that receives the motor therein. The tissue-removing element can include a distal tip that extends distally beyond the motor to define the distal end of the catheter. The motor can be controlled using an actuator located outside the body. And in some embodiments, use of the catheter involves adjusting the rotational speed of the tissue-removing element using the actuator.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
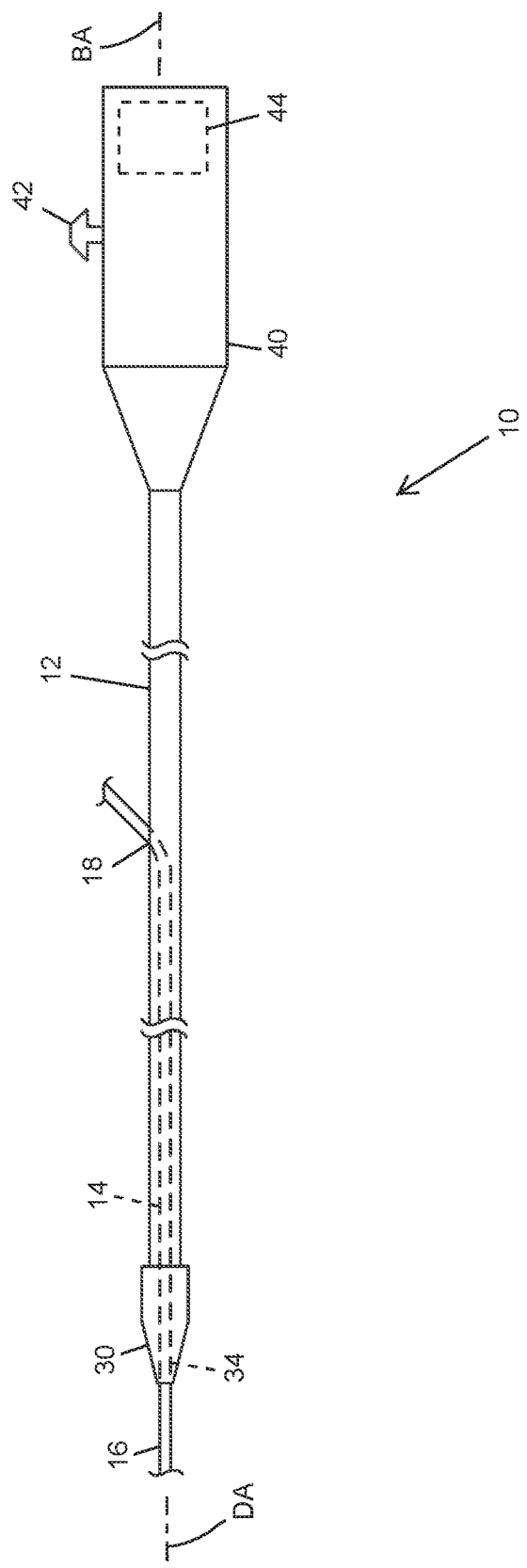
FIG. 1 is a schematic illustration of a catheter.

Referring to the drawings, a rotational tissue-removing catheter for removing tissue in a body lumen is generally indicated at reference number 10. The illustrated catheter 10 is suitable for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., peripheral arterial or peripheral venous wall, etc.). Features of the disclosed embodiments may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

In some embodiments, the catheter 10 is sized for being received in a peripheral blood vessel of a subject. Thus, the catheter 10 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

The catheter 10 comprises an elongate body 12 having an axis BA and proximal and distal end portions spaced apart along the axis. The body 12 is sized and shaped for insertion into a body lumen of a subject. The elongate body 12 defines a guidewire lumen 14 for slidably receiving a guidewire 16 therein so that the catheter 10 can be advanced through the body lumen by traveling along the guidewire. In certain embodiments, the elongate body 12 may have a lubricious inner surface for sliding over the guidewire 16 (e.g., a lubricious surface may be provided by a lubricious polymer layer or a lubricious coating). In the illustrated embodiment, the elongate body 12 defines a rapid exchange guidewire lumen 14. The guidewire lumen 14 extends through the distal end portion of the elongate body 12 and through a guidewire exchange port 18 formed in the side wall of the elongate body 12. The guidewire exchange port 18 communicates with the guidewire lumen 14 and extends generally transverse to the axis BA of the elongate body 12 at a location spaced apart between the proximal end portion and the distal end portion of the elongate body. The guidewire exchange port 18 allows the catheter 10 to be used in a rapid exchange and single operator exchange procedures.

Figure 2:
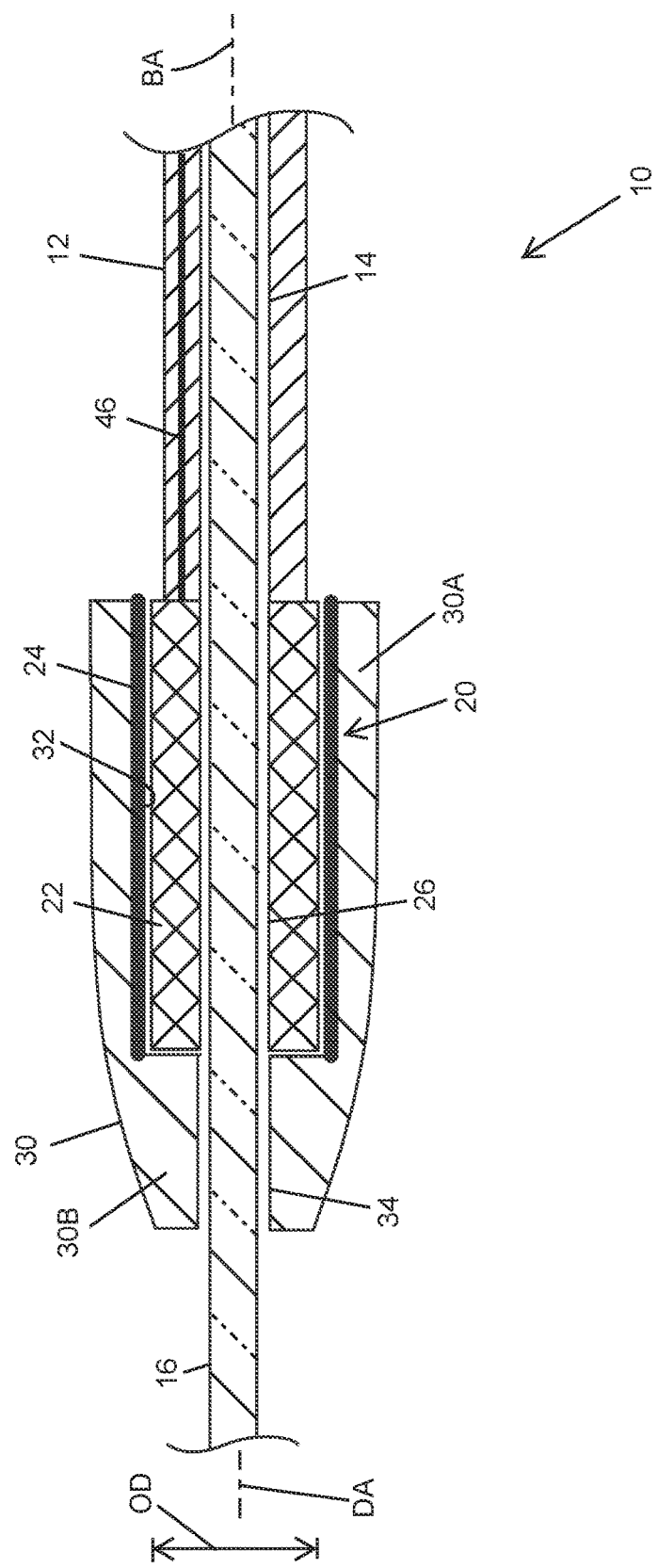
FIG. 2 is an enlarged schematic fragmentary longitudinal cross section of a distal end portion of the catheter.

Referring to FIG. 2, a motor, generally indicated at 20, is fixed to the distal end portion of the elongate body 12. The motor 20 has a proximal end portion adjacent the distal end portion of the elongate body 12, a distal end portion that is spaced apart distally from the distal end portion of the elongate body, and a perimeter that extends generally along a drive axis DA of the motor between the proximal and distal end portions. The motor 20 comprises a stator 22 that is fixed to the distal end portion of the elongate body 12. A rotor 24 of the motor (which in one embodiment defines a circumferential casing about the stator 22) is mounted on the stator for rotation with respect to the stator and the elongate body about the drive axis DA. In the illustrated embodiment, the motor 20 is mounted on the elongate body 12 so that the drive axis DA is coincident with the axis BA of the elongate body. In other embodiments, the motor could be mounted on the elongate body so that the drive axis is spaced radially apart from or transverse to the axis BA of the elongate body.

The motor 20 comprises a micro-motor that is sized and arranged for being received in the body lumen of the subject. In one embodiment, the motor 20 has an outer diameter OD from about 0.5 mm to about 4 mm, or from about 0.5 mm to about 3 mm, or from about 0.5 mm to about 2 mm, or from about 0.5 mm to about 1 mm, or from about 0.75 mm to about 4 mm, or from about 0.75 mm to about 3 mm, or from about 0.75 mm to about 2 mm, or from about 0.75 mm to about 1 mm, or from about 1 mm to about 4 mm, or from about 1 mm to about 3 mm, or from about 1 mm to about 2 mm, or about 1.25 mm. In the illustrated embodiment, the motor 20 is cannulated. For example, the motor 20 may be a through-hole electric motor. The motor 20 defines a guidewire lumen 26 extending along the drive axis DA from the proximal end portion through the distal end portion of the motor. The guidewire lumen 26 of the motor 20 is aligned with the guidewire lumen 14 of the elongate body 12 so that the guidewire 16 extends from the distal end portion of the elongate body into the guidewire lumen of the motor without bending, curving, or changing directions.

A tissue-removing element 30 extends along the drive axis DA from a proximal end adjacent the distal end portion of the elongate body 12 to an opposite distal end. The tissue-removing element 30 is operatively connected to the motor 20 for being selectively rotated by the motor about the drive axis DA. When the catheter 10 is inserted into the body lumen and the motor 20 is rotating the tissue-removing element 30, the tissue-removing element is configured to remove occlusive tissue in the body lumen to separate the tissue from the wall of the body lumen.

The tissue-removing element 30 has a proximal end and a distal end spaced apart from one another along the drive axis DA. In one embodiment, the tissue-removing element 30 is integrally formed with the rotor 24 of the motor 20. In other embodiments, the tissue-removing element 30 is separately attached to the rotor 24 for conjoint rotation with the rotor about the stator 22. Any suitable tissue-removing element for removing tissue in the body lumen as it is rotated may be used in one or more embodiments. In the illustrated embodiment, the tissue-removing element 30 comprises an abrasive burr configured to abrade tissue in the body lumen when the motor 20 rotates the abrasive burr about the drive axis DA. The abrasive burr 30 has an abrasive outer surface formed, for example, by a diamond grit coating, surface etching, or the like. In other embodiments, the tissue-removing element can comprise one or more cutting elements having smooth or serrated cutting edges, a macerator, a thrombectomy wire, etc.

The illustrated tissue-removing element 30 has a proximal mounting portion 30A and a distal tip portion 30B. The mounting portion 30A defines a cavity 32 for receiving at least a portion of the motor 20 (e.g., the stator 22, an axial segment of the stator, etc.) therein. The cavity 32 extends through the proximal end of the tissue-removing element 30 such that the tissue-removing element defines an opening at its proximal end. In the illustrated embodiment, the proximal end of the motor 20 is substantially aligned with the proximal end of the tissue-removing element 30 along the drive axis DA. But in other embodiments, the proximal end of the motor can protrude outwardly or be recessed inwardly from the proximal end of the tissue-removing element. The distal tip portion 30B of the tissue-removing element 30 defines a distal end of the cavity 32. Accordingly, the tissue-removing element 30 is shaped and arranged to extend around at least a portion of the perimeter of the motor 20 and thus provides a relatively compact assembly for driving rotation and abrading tissue at the distal end portion of the catheter 10.

The distal tip portion 30B of the tissue-removing element 30 extends distally from the motor 20 along the drive axis DA. The diameter of the distal tip portion 30B tapers distally from the motor 20 and defines a distally tapering segment of the tissue-removing element 30. The tapered distal tip portion 30B therefore has a general wedge shape configured for wedging apart constricted tissue passages as it simultaneously opens the passage by removing tissue using the abrasive action of the burr 30. The distal tip portion 30B of the tissue-removing element 30 defines a guide wire lumen 34 that extends from a proximal opening aligned with the guidewire lumen 26 of the motor 20 through the distal end of the tissue-removing element. Each of the guidewire lumens 14, 26, 34 is substantially aligned along the axis BA of the elongate body 12 of the catheter 10. In use, the guidewire 16 extends from the distal end portion of the elongate body 12, into the guidewire lumen 26 of the motor 20, and through the guidewire lumen 34 of the tissue-removing element 30, without bending, curving, or changing directions.

As shown in FIG. 1, the catheter 10 comprises a handle 40 secured to the proximal end portion of the elongate body 12. The handle 40 supports an actuator 42 (e.g., a lever, a button, a dial, a switch, or other device) configured for selectively actuating the motor 20 from a location outside the body lumen (e.g., remote from the motor) to selectively drive rotation of the tissue-removing element 30. In one or more embodiments, the actuator 42 is positioned on the handle 40 for movement relative to the handle to selectively couple the motor 20 to a power supply 44 (e.g., battery supply) supported by the handle 40. The actuator 42 selectively conveys power from the power supply 44 to the motor 20 over a conductor 46 (FIG. 2) extending longitudinally within the body 12. In exemplary embodiments, the actuator 42 is movable with respect to the handle 40 to a non-actuating position and a plurality of actuated positions for variably adjusting the speed of the motor 20. In the non-actuated position, the actuator 42 prevents the motor 20 from drawing power from the power supply 44 and thus prevents the motor from rotating the tissue-removing element 30. In each of the actuated positions, the actuator 42 controls various amounts of power being delivered to the motor 20 from the power supply 44 to adjust the speed at which the motor rotates the tissue-removing element 30. In some embodiments, the actuator 42 is further configured to selectively reverse the polarity of the power supplied to the motor 20 to reverse the direction the motor rotates the tissue-removing element 30 about the drive axis DA. It is understood that other suitable actuators, including but not limited to touchscreen actuators, wireless control actuators, automated actuators directed by a controller, etc., may be suitable to selectively actuate and/or adjust the speed of a distally positioned motor in other embodiments. In some embodiments, the motor 20 may draw power from a power supply located adjacent the distal end portion of the catheter 10. In other embodiments, the power supply may come from an external source.

Referring to FIGS. 1 and 2, to remove tissue in the body lumen of a subject, a practitioner inserts the guidewire 16 into the body lumen of the subject, to a location distal of the tissue that is to be removed. Subsequently, the practitioner inserts the proximal end portion of the guidewire 16 through the guidewire lumen 34, the guidewire lumen 26, and the guidewire lumen 14 so that the guidewire extends through the rapid exchange port 18. With the catheter 10 loaded onto the guidewire 16, the practitioner advances the elongate body 12 along the guidewire until the tissue-removing element 30 is positioned proximal and adjacent the tissue. When the tissue-removing element 30 is positioned proximal and adjacent the tissue, the practitioner actuates the motor 20 using the actuator 42 (which is positioned outside the body lumen on the handle 40) to rotate the tissue-removing element. The tissue-removing element 30 abrades (or otherwise removes) the tissue in the body lumen as it rotates about the drive axis DA. While the tissue-removing element 30 is rotating, the practitioner selectively moves the catheter 10 distally along the guidewire 16 to abrade the tissue and, for example, increase the size of the passage through the body lumen. The practitioner may also move the catheter 10 proximally along the guidewire 16, and may repetitively move the catheter in distal and proximal directions to obtain a back-and-forth motion of the tissue-removing element 30 across the tissue. In addition, the practitioner may selectively change the position of the actuator 42 to adjust the speed of the motor 20 to the desired speed for abrading or otherwise removing the tissue in the body lumen. When the practitioner is finished using the catheter 10, the catheter can be withdrawn from the body lumen and unloaded from the guidewire 16 by sliding the catheter proximally along the guidewire 16. Because the elongate body 12 includes the rapid exchange port 18 at the intermediate location along the length of the catheter 10, a single practitioner can exchange the catheter 10 (e.g., the catheter can be exchanged for another type of catheter, for another ablation catheter with a larger tissue-removing element, etc.) without assistance.

As can be seen, therefore, the illustrated catheter 10 combines the advantages of a rotational tissue-removing device with a rapid exchange catheter. The rapid exchange guidewire lumen 14 in the rotational tissue-ablation catheter 10 can be provided because the rotational drive components of the catheter 10 are located at the distal end portion of the elongate body 12. Thus, the catheter 10 does not require an elongate rotational driveshaft that extends along the elongate body 12 and would otherwise interfere with the guidewire 16 extending radially through the rapid exchange port 18. Since the elongate body 12 does not require a rotational driveshaft, it can be optimized for pushability and tracking characteristics, instead of drive transmission characteristics. For example, in one embodiment the elongate body 12 comprises a reinforcing braid (e.g., a high strength fiber braid embedded in a polymer). Other elongate bodies can be formed of other materials.

Moreover, because the only part of the catheter 10 that rotates about the guidewire 16 is the tissue-removing element 30, friction between the catheter 10 and the guidewire is greatly reduced in comparison with tradition rotational tissue-removing devices. Furthermore, because of the low rotational friction, the catheter 10 has broad guidewire compatibility. And since no rotational drive shaft is required, the elongate body 12 can be optimized for pushing and tracking instead of drive transmission, thereby enhancing the pushing and tracking characteristics in comparison with conventional rotational tissue-removing catheters.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:
   an elongate body having an axis, and proximal and distal end portions spaced apart from one another along the axis, wherein the elongate body is sized and shaped to be received in the body lumen;
   a motor fixed to the distal end portion of the elongate body and having a drive axis and a perimeter extending around and along the drive axis; and
   a tissue-removing element extending around at least a portion of the perimeter of the motor and operatively connected to the motor for being selectively rotated by the motor about the drive axis, the tissue-removing element being configured to remove the tissue as the tissue-removing element is rotated by the motor within the body lumen,
   wherein the tissue-removing element defines a cavity extending along the drive axis, the motor being received in the cavity.

2. A tissue-removing catheter as set forth in claim 1, wherein the tissue-removing element has a proximal end and a distal end spaced apart along the drive axis, the cavity extending through the proximal end of the tissue-removing element.

3. A tissue-removing catheter as set forth in claim 2, wherein the motor has a proximal end and a distal end spaced apart along the drive axis, the proximal ends of the motor and the tissue-removing element being substantially aligned along the drive axis.

4. A tissue-removing catheter as set forth in claim 1, wherein the tissue-removing element includes a distal tip portion defining a distal end of the cavity.

5. A tissue-removing catheter as set forth in claim 1, wherein the tissue-removing element has a proximal end and a distal end spaced apart along the drive axis and comprises a distally tapered tip segment adjacent the distal end.

6. A tissue-removing catheter as set forth in claim 1, wherein the motor is cannulated.

7. A tissue-removing catheter as set forth in claim 1, wherein the elongate body defines a guidewire lumen.

8. A tissue-removing catheter as set forth in claim 7, wherein the guidewire lumen extends through the distal end portion of the elongate body.

9. A tissue-removing catheter as set forth in claim 7, wherein the elongate body defines a guidewire exchange port communicating with the guidewire lumen and extending transverse to the axis of the elongate body at a location spaced apart between the proximal end portion and the distal end portion of the elongate body.

10. A tissue-removing catheter as set forth in claim 7, wherein each of the motor and the tissue-removing element defines a guidewire lumen, the guidewire lumens of the motor, the tissue-removing element, and the elongate body being substantially aligned.

11. A tissue-removing catheter as set forth in claim 1, wherein the tissue-removing element comprises an abrasive burr.

12. A tissue-removing catheter as set forth in claim 1, further comprising an actuator remote from the motor configured to selectively actuate the motor to drive rotation of the tissue-removing element.

13. A tissue-removing catheter as set forth in claim 12, further comprising a handle secured to the proximal end portion of the elongate body, the actuator being positioned on the handle.

14. A tissue-removing catheter as set forth in claim 12, wherein the actuator is configured to selectively adjust a speed of the motor.

15. A tissue-removing catheter for removing tissue in a body lumen, the tissue-removing catheter comprising:
   an elongate body having an axis and a proximal end portion and a distal end portion spaced apart from one another along the axis;
   a motor fixed to the distal end portion of the elongate body and having a drive axis; and
   a tissue-removing element extending distally from the motor along the drive axis and operatively connected to the motor for being selectively driven by the motor in rotation about the drive axis, the tissue-removing element being configured to remove the tissue as the tissue-removing element is rotated by the motor within the body lumen, wherein the tissue-removing element comprises a distal tip portion extending distally from the motor along the drive axis and a proximal mounting portion aligned with the motor along the drive axis.

16. A tissue-removing catheter as set forth in claim 15, wherein the mounting portion of the tissue-removing element includes a receptacle receiving the motor therein.

17. A tissue-removing catheter as set forth in claim 15, wherein the tissue-removing element tapers inward as it extends distally from the motor.

18. A method of removing tissue in a body lumen, the method comprising:

advancing an elongate body through the body lumen to position a distal end portion of the elongate body adjacent the tissue and a proximal end portion of the elongate body outside of the body lumen;

using an actuator outside the body lumen to actuate a motor mounted on the distal end portion of the elongate body and located inside the body lumen to rotate a tissue-removing element about a drive axis of the motor to remove the tissue, wherein the tissue-removing element defines a cavity extending along the drive axis, the motor being received in the cavity; and using the actuator outside the body lumen to adjust a speed of the motor inside the body lumen.

\* \* \* \* \*